(12) United States Patent
Rane et al.

(10) Patent No.: US 6,284,481 B1
(45) Date of Patent: Sep. 4, 2001

(54) ASSAY

(75) Inventors: Rajendra Rane, Maharashtra St; Santanu Datta, Bangalore, both of (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/530,250
(22) PCT Filed: Feb. 1, 2000
(86) PCT No.: PCT/SE00/00208
 § 371 Date: Apr. 26, 2000
 § 102(e) Date: Apr. 26, 2000
(87) PCT Pub. No.: WO00/46396
 PCT Pub. Date: Aug. 10, 2000

(30) Foreign Application Priority Data

Feb. 2, 1999 (IN) .............................................. 121/MAS/99
Feb. 12, 1999 (SE) .................................................... 9900466

(51) Int. Cl.$^7$ ............................... C12Q 1/37; C12Q 1/00; G01N 33/72
(52) U.S. Cl. .................................... 435/23; 435/4; 436/66
(58) Field of Search ........................... 435/23, 4; 436/66

(56) References Cited

FOREIGN PATENT DOCUMENTS

WO-200028391A 8/2000 (WO) .

OTHER PUBLICATIONS

Goldberg et al., J. Exp. Med., 1991, 173(4), 961–969.
Brindley, P.J., Mol. Biochem. Parasitol., 1997, 89(1), 1–9.
Ridley, R., J. Pharm. Pharmacol., 1997, 49(2), 43–48.
Hill et al., FEBS Lett., 1994, 352(2), 155–158.

* cited by examiner

Primary Examiner—Louise N. Leary
(74) Attorney, Agent, or Firm—White & Case LLP

(57) ABSTRACT

The present invention provides a spectrophotometric assay for detecting hemoglobin degradation.

9 Claims, 2 Drawing Sheets

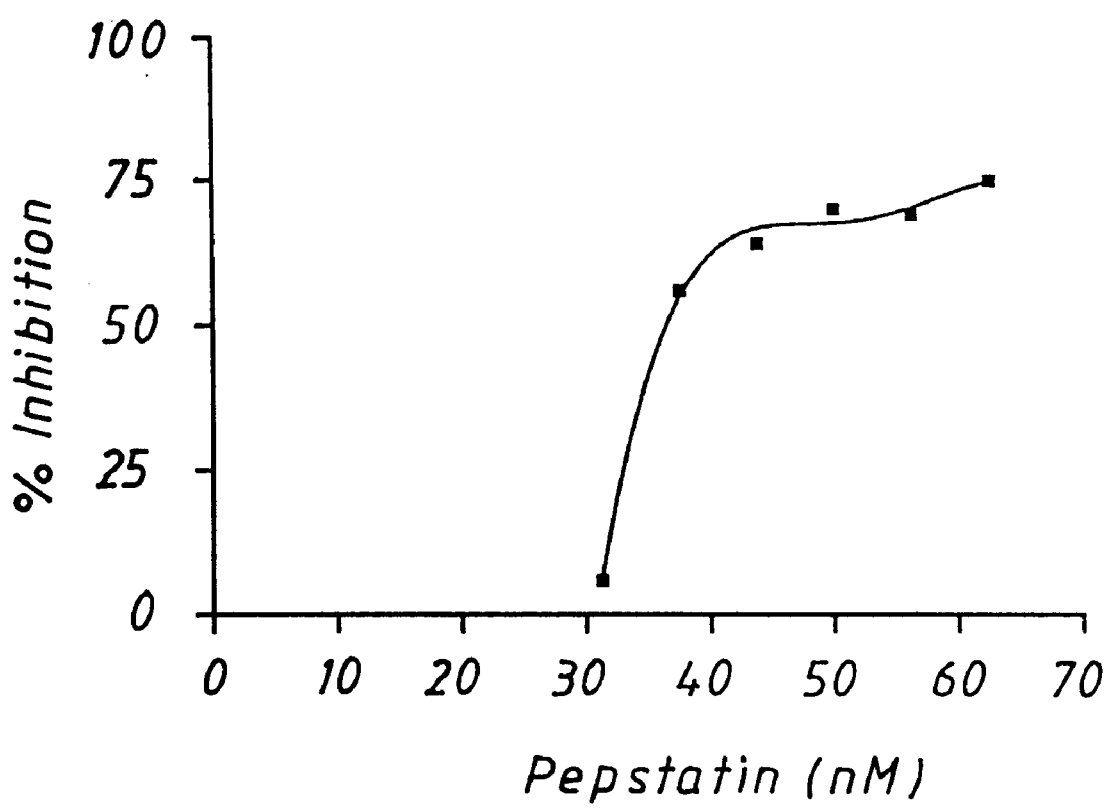

ASSAY

The present invention relates to an assay for detecting hemoglobin degradation.

Several parasites are known to degrade host cell hemoglobin by means of their proteases, for example, the human malarial parasite *Plasmodium falciparum*. It has a limited capacity to de novo synthesize amino acids or to take them up from its immediate environment. Thus, this parasite uses the host erythrocyte hemoglobin as a major nutrient source. It consumes 25%–75% of the host cell hemoglobin during a short segment of its intra-erythrocytic life cycle. This massive catabolism is probably an ordered process which occurs in a unique acidic organelle called the digestive vacuole, at a pH optimum of ~5. At least three vacuolar proteases (two aspartic and one cysteine) are known to be involved in the breakdown of human hemoglobin to its constituent amino acids. One of the aspartic proteases, Plasmepsin I has been indicated in the initiation of hemoglobin degradation by making the first cleavage and unwinding the molecule, so that further proteolysis can proceed efficiently. A second aspartic protease, Plasmepsin II presumably cleaves hemoglobin with an overlapping specificity. The cysteine protease, Falcipain is also involved in an early step of hemoglobin degradation. All three proteases Plasmepsin I, II & Falcipain cleave denatured hemoglobin in vitro.

Several different assays exist for monitoring hemoglobin degradation by parasitic proteases, e.g. as described by Daniel E. Goldberg et al. in "Hemoglobin degradation in the malaria parasite *Plasmodium falciparun*: An ordered process in a unique organelle", Biochemistry (1990), 87:2931–2935.

For example, there is the Centricon Assay for Proteolysis in which varying concentrations of enzyme (protease) extract are added to an incubation mixture containing radioactively labelled [$^3$H] hemoglobin and sodium citrate buffer (pH 5). After incubation at 37° C. for one hour, the reaction is stopped by addition of iced guanidine hydrochloride. After 15 minutes on ice, the mixture is loaded onto a Centricon 10 kDa filter and centrifuged at 5000 g for one hour. The filtrate is then assayed for radioactivity. The assay has been shown to be linear with time and protein concentration.

In the Trichloroacetic Acid (TCA) Assay for Proteolysis hemoglobin degradation is assessed by measuring production of TCA-soluble fragments. The Centricon assay incubation mix is used with citrate/phosphate buffer at varying pH. TCA precipitation is performed by addition of iced unlabelled hemoglobin and iced 20% TCA. After 30 minutes on ice, the mixture is centrifuged at 16,000 g for 15 minutes and the supernatant is assayed for radioactivity.

Hemoglobin degradation may also be assessed using SDS-PAGE Analysis. Human hemoglobin is used as a substrate in the Centricon assay incubation mix. The reaction is stopped by adding SDS sample buffer and boiling for 3 minutes. The samples are then run on a 20% SDS-PAGE which is developed using Silver Staining.

All of the above known assay systems have the drawback that they serve only as end-point assays. Furthermore, because of their nature, such assays are often time consuming.

Assays in which the proteolytic activities of the parasitic proteases can be monitored continuously and directly are also known in the art. These assays employ synthetic substrates, mostly oligo-peptides or peptidomimics, that are designed to simulate the natural cleavage sites of a given protease, e.g., Plasmepsin II as described by Jeffrey Hill et al. in "High level expression and characterisation of Plasmepsin II, an aspartic proteinase from *Plasmodium falciparum*", Federation of European Biochemical Societies (FEBS) Letters (1994), 352:155–158.

Whilst such assays using synthetic substrates have the benefit that they are generally quicker to carry out than those mentioned above in which hemoglobin is used as the substrate, the synthetic substrates are expensive and are required in high concentration. Furthermore, in the context of ligand binding studies, it has been found that these assays only work well with pure ligands and not ligand mixtures.

Therefore, it would be desirable to develop an assay for detecting hemoglobin degradation that is quick and efficient, that uses hemoglobin as the substrate and that can be reliably used with a variety of ligand sources.

In accordance with the present invention, there is provided a spectrophotometric assay for detecting hemoglobin degradation which comprises:

a) preparing a mixture comprising hemoglobin and a proenzyme of a hemoglobin-degrading enzyme, wherein the mixture has a pH in the range from 7.5 to 7.6, b) measuring the absorbance of the mixture at a wavelength ($\lambda$) in the range from 404 to 407 nm, c) acidifying the mixture to activate the hemoglobin-degrading enzyme, d) incubating the mixture of step c), e) measuring the absorbance of the mixture of step d) at a wavelength ($\lambda$) in the range from 404 to 407 nm, f) adding a base to the mixture of step e) to effect renaturation of undegraded hemoglobin, g) incubating the mixture of step f), and h) measuring the absorbance of the mixture of step g) at a wavelength ($\lambda$) in the range from 404 to 407 nm.

The present assay is based on and makes use of the spectral properties of hemoglobin. The tetra-pyrrole nucleus of hemoglobin is responsible for a characteristic absorption band between 400 to 410 nm exhibited by hemoproteins, and this is referred to as the Soret band. Human hemoglobin, in its native form, absorbs at a wavelength ($\lambda_{max}$)=405 to 406 nm. In step a) of the assay, the hemoglobin is present in its native state. On addition of acid in step c), the proenzyme is converted to active hemoglobin-degrading enzyme and the hemoglobin is partially denatured. Upon activation, the hemoglobin-degrading enzyme begins to cleave the partially denatured hemoglobin resulting in removal of the heme moiety and an observed drop in absorbance at 405 to 406 nm. Base is added in step f) to effect renaturation of undegraded hemoglobin (the term "undegraded hemoglobin" meaning hemoglobin that has not been cleaved by the hemoglobin-degrading enzyme), resulting in an observed increase in absorbance at 405 to 406 nm. By monitoring the changes in absorption in the range from 404 to 407 nm, the present assay provides a direct method for assessing hemoglobin degradation.

FIG. 3 illustrates the inhibition of Plasmepsin II by the enzyme inhibitor, Pepstatin, as determined by the assay according to the invention.

In step a) of the assay, it is preferred if mammalian, especially human, hemoglobin is used. Furthermore, in principle, the proenzyme of any enzyme that is capable of degrading mammalian hemoglobin may be used including aspartic proteases such as cathepsin D, trypsin and chymotrypsin. However, it is preferred if the proenzyme of Plasmepsin I, Plasmepsin II or Falcipain is used. The proenzyme of Plasmepsin II is particularly preferred.

The pH of the mixture formed in step a) is in the range from 7.5–7.6. It should be understood that under the pH conditions used in step a) most, if not all, of the proenzyme is stable and there is little or no hemoglobin-degrading enzyme activity.

In step c) of the assay, the mixture is acidified using, for example, a weak organic acid such as citric acid, typically in aqueous solution, to effect maximum conversion of the proenzyme to active hemoglobin-degrading enzyme. The pH of the acidified mixture will preferably be in the range from 4.5 to 5, and is especially 4.7.

In both steps d) and g), incubation is preferably carried out at a temperature in the range from 20° C. to 37° C. for a period of time in the range from 20 to 90 minutes, e.g. at 37° C. for 40 minutes.

The base used in step f) is preferably a weak organic base such as unbuffered Tris(hydroxymethyl)aminomethane (Tris base). The base is conveniently used in aqueous solution.

The assay of the present invention may be used to screen for ligands, in particular inhibitors, of hemoglobin-degrading enzymes and, accordingly, the mixture prepared in step a) may further comprise a candidate ligand. Since degradation of hemoglobin is necessary for the growth of erythrocytic malarial parasites such as *Plasmodium falciparum*, Plasmepsin I, Plasmepsin II and Falcipain therefore represent very good targets for the development of anti-malarial drugs. In this regard, it is to be noted that the present assay has the advantage that it can be readily adapted for robotics automation and hence for high throughput screening.

The present invention will now be further explained by reference to the following illustrative examples.

Figure 1:
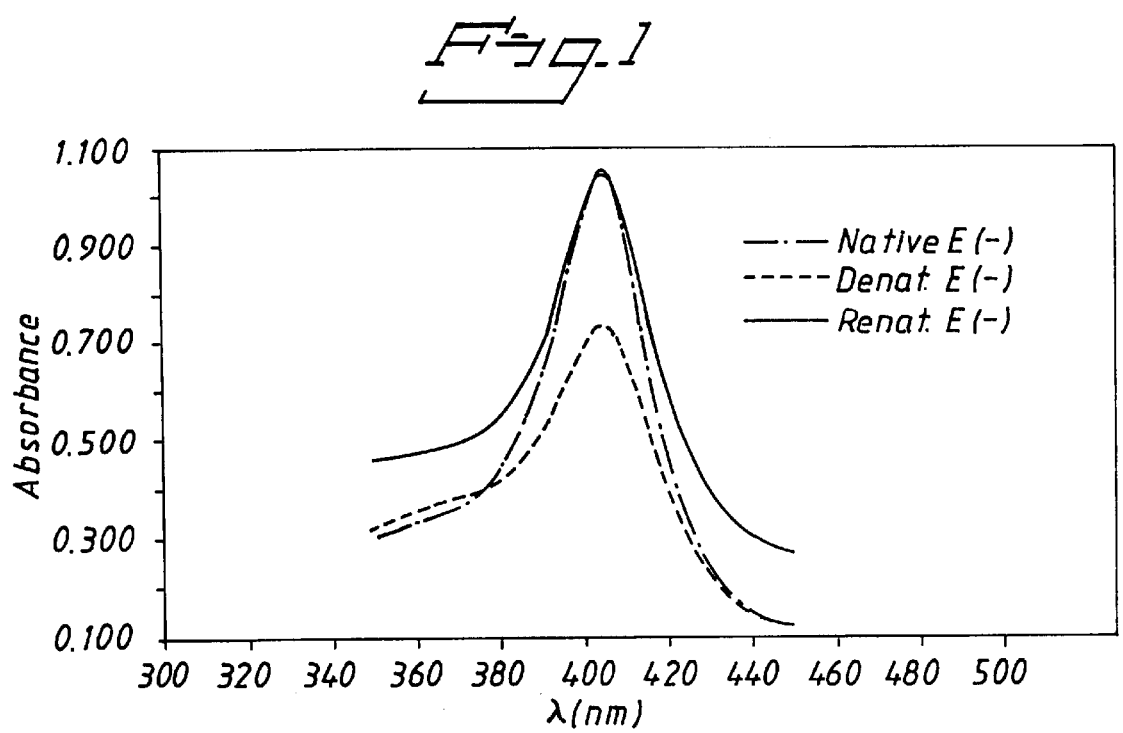
FIG. 1 illustrates the spectral properties of native, denatured and prenatured forms of human hemoglobin.

EXAMPLE 1
Spectral properties of native, denatured & renatured forms of human hemoglobin 20 μl of human hemoglobin (Hb) solution (5 mg/ml) along with 180 μl of 10 mM Tris HCl (pH 7.5) buffer were added to 5 wells in a 96-well microtitre plate. The absorption spectra (range 350–550 nm) were read in the SpectraMax 190 (Molecular Devices Inc., USA) spectrophotometer, against a blank consisting of the buffer alone. After recording the native hemoglobin spectrum, 50 μl of 7.57 mM citric acid were added to the wells. The plate was shaken for 45 seconds in the spectrophotometer and then incubated at 37° C. The absorption spectra of the denatured hemoglobin were read after 40 minutes of incubation. Thereafter, 50 μl of 25 mM unbuffered solution of Tris base were added to the wells. The spectra of renatured hemoglobin were read after 40 minutes of incubation at 37° C. In this experiment, $\lambda_{max}$ of native, denatured and renatured hemoglobin solutions were recorded and are shown in FIG. 1. It will be noted from FIG. 1 and also from Table I below that both native and renatured Hb have identical $\lambda_{max}$ i.e. 405–406 nm.

TABLE I

| | $\lambda_{max}$ (nm) | Extent of Renaturation |
|---|---|---|
| Native Hb (pH 7.5) | 405–406 | |
| Denatured Hb | 360 | |
| Renatured Hb | 405–406 | 99.5% |

This experiment clearly indicates that the denaturation and renaturation of human hemoglobin can be monitored spectrophotometrically at $\lambda_{max}$=405–406 nm.

The molar extinction coefficient $\epsilon_M$ of human hemoglobin at $\lambda_{max}$. (406 nm) was found to be 276069.66 cm$^{-1}$. M$^{-1}$ which is a reflection of its strong native absorbance at that wavelength.

EXAMPLE 2
Assay based on Plasmepsin II according to the invention

20 μl of human hemoglobin solution (5 mg/ml) along with 180 μl of 10 mM Tris HCl (pH 7.5) buffer were added to two sets of wells (5 wells/set ) in a 96-well microtitre plate. The absorption spectra (range 350–550 nm) were read in the SpectraMax 190 (Molecular Devices Inc., USA) spectrophotometer, against a blank consisting of the buffer alone. At this point in time, in one set of wells, 400 ng of (1 μl) of Plasmepsin II (in proenzyme form) were added. The other set of wells received just 1 μl buffer. This was followed by the addition of 50 μl of 7.57 mM citric acid to each well. The plate was shaken for 45 seconds in the spectrophotometer and then incubated at 37° C. The absorption spectra of the denatured hemoglobin were read after 40 minutes of incubation. Thereafter, 50 μl of 25 mM unbuffered solution of Tris base were added to each well. The spectra of renatured hemoglobin were read after 40 minutes of incubation at 37° C. The results obtained are shown in FIG. 2.

Figure 2:
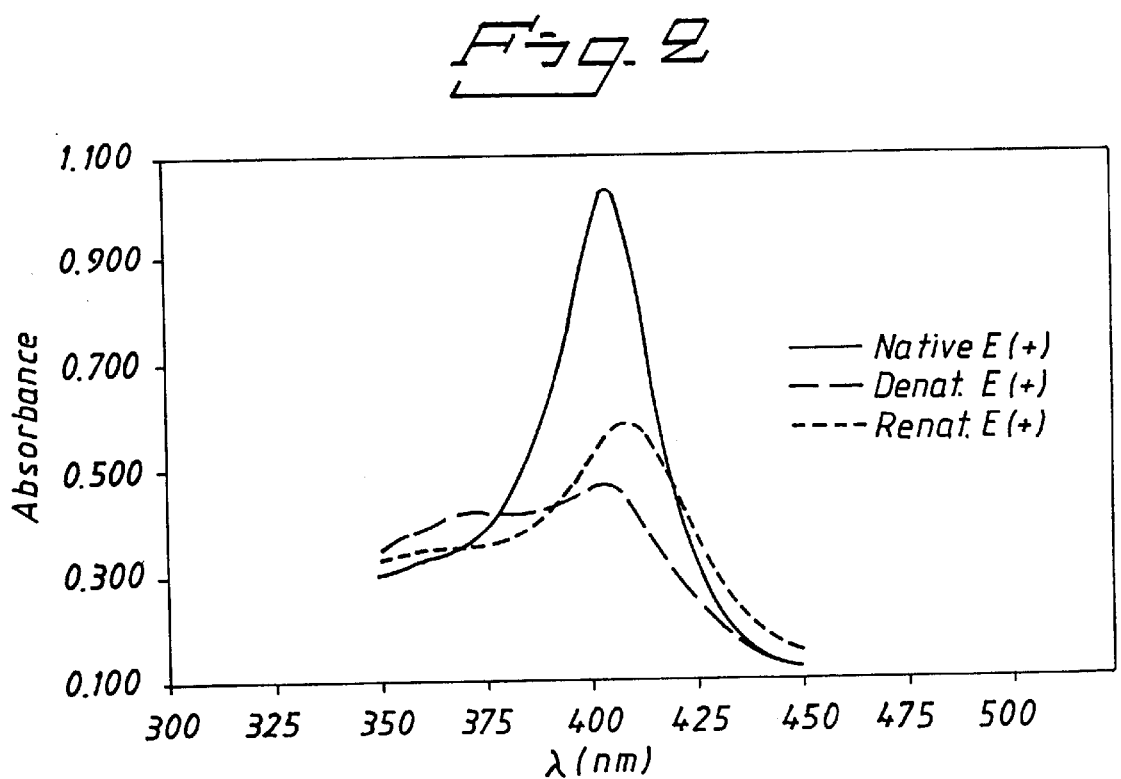
FIG. 2 illustrates the effect of Plasmepsin II-mediated proteolytic degradation on the spectral properties of human hemoglobin.

In FIG. 2, the decrease in the absorbance at λ=406 nm is a result of two phenomena: (1) denaturation of hemoglobin because of acidic pH, and (2) degradation of hemoglobin due to Plasmepsin II-mediated proteolysis. The rate of degradation of hemoglobin due to Plasmepsin II can be deduced from the difference between the denaturation rate and the renaturation rate.

To verify that this difference indicates the true degradation rate, renaturation of the hemoglobin in the presence and absence of Plasmepsin II was checked. In principle, if hemoglobin is degraded, it will not renature back to the fullest extent as compared to the control without enzyme and this is confirmed by the data presented in Table II following:

TABLE II

| | Without Plasmepsin II, E(−) Absorbance (A) at 406 nm | With Plasmepsin II, E(+) Absorbance (A) at 406 nm |
|---|---|---|
| Native Hb | 1.048 | 1.025 |
| Denatured Hb | 0.734 | 0.463 |
| Renatured Hb | 1.043 | 0.574 |

% Recovery in E(−) cuvette: 1.043−0.734=0.309A=100%

% Recovery in E(+) cuvette: 0.574−0.463=0.111A=35.9%

Hemoglobin degraded by Plasmepsin II=100−35.9=64.1%

This experiment clearly demonstrates that Plasmepsin II-mediated hemoglobin degradation is responsible for the failure to regain total renaturation.

EXAMPLE 3
HTS Assay Format

The assay described in Example 2 above was modified to suit high throughput screening (HTS) of Plasmepsin II inhibitors using 96-well microtitre plates but 384-well microtitre plates could also have been used.

In a 96-well microtitre plate 16 wells were used for appropriate controls and 80 wells were used for ligand testing. All of the 96 wells were individually filled with 195 μl assay mix which comprised a buffered solution of human hemoglobin (6 μM, pH=7.6) with or without enzyme. All of the wells, except the 0% reaction controls, received Plasmepsin II (in proenzyme form: 8 μl diluted: 0.4 μg/well). Of the control wells, 6 wells contained no Plasmepsin II proenzyme (0% reaction controls) and 6 wells contained Plasmepsin II proenzyme (100% reaction controls). Each of these 12 control wells contained 5 μl dimethyl sulfoxide (DMSO). Also, another 4 control wells contained 5 μl Pepstatin (Standard Inhibitor controls). The remaining 80 wells contained 5 μl solution of candidate ligand in DMSO.

The initial absorbance (I) of each well was read at 406 nm. Then 50 μl of 7.57 mM citric acid was added to each well so that the pH of the reaction mixture was lowered from 7.6 to 4.7. The plate was incubated at 37° C. for 40 minutes and absorbance readings were once more taken at 406 nm. Thereafter, 50 μl of 25 mM unbuffered Tris base solution was added to each well and the plate incubated at 37° C. for a further 40 minutes. At the end of this incubation period, final absorbance readings (F) were taken at 406 nm.

The "Activity Window" (AW), which is a measure of the proteolytic activity of the hemoglobin-degrading enzyme, can be determined according to the following equation:

$$AW = \text{absolute } [\text{average}(I-F)_{0\% \text{ reaction control}} - \text{average } (I-F)_{100\% \text{ reaction control}}].$$

Although just the final absorbance difference between the 0% reaction control (without enzyme) and the 100% reaction control (with enzyme) wells can alone define the activity window, initial reading is necessary to correct for the initial optical density differences that may occur between the 0% and 100% reaction control wells. Also, when assessing the percentage (%) inhibition of hemoglobin-degrading enzyme by a given candidate ligand, such a procedure takes care of the possible optical density contribution due to the candidate ligand. The activity window for Plasmepsin II is normally in the region of 0.4 under the aforesaid conditions.

FIG. 3 shows the inhibition of Plasmepsin II by the enzyme inhibitor, Pepstatin, as determined by the assay according to the invention.

What is claimed is:

1. A spectrophotometric assay for detecting hemoglobin degradation which comprises:
    a) preparing a mixture comprising hemoglobin and a proenzyme of a hemoglobin-degrading enzyme, wherein the mixture has a pH in the range from 7.5 to 7.6,
    b) measuring the absorbance of the mixture at a wavelength (λ) in the range from 404 to 407 nm,
    c) acidifying the mixture to activate the hemoglobin-degrading enzyme,
    d) incubating the mixture of step c),
    e) measuring the absorbance of the mixture of step d) at a wavelength (λ) in the range from 404 to 407 nm,
    f) adding a base to the mixture of step e) to effect renaturation of undegraded hemoglobin,
    g) incubating the mixture of step f), and
    h) measuring the absorbance of the mixture of step g) at a wavelength (λ) in the range from 404 to 407 nm.

2. An assay according to claim 1, wherein in step a) human hemoglobin is used together with the proenzyme of Plasmepsin I, Plasmepsin II or Falcipain.

3. An assay according to claim 1 or claim 2, wherein in step c) a weak organic acid is used to acidify the mixture.

4. An assay according to claim 3, wherein the organic acid is citric acid.

5. An assay according to claim 1, wherein the acidified mixture of step c) has a pH in the range from 4.5 to 5.

6. An assay according to claim 1, wherein a weak organic base is used in step f).

7. An assay according to claim 6, wherein the base is Tris(hydroxymethyl)aminomethane.

8. An assay according to claim 1, wherein the mixture of step a) further comprises a candidate ligand.

9. An assay according to claim 8, wherein the candidate ligand is an inhibitor of the hemoglobin-degrading enzyme.

* * * * *